(12) United States Patent
Frazier

(10) Patent No.: US 8,708,919 B1
(45) Date of Patent: Apr. 29, 2014

(54) SYSTEM AND METHOD FOR REMOTELY SENSING VITAL SIGNS

(75) Inventor: Gary A. Frazier, Garland, TX (US)

(73) Assignee: Raytheon Company, Waltham, MA (US)

( * ) Notice: Subject to any disclaimer, the term of this patent is extended or adjusted under 35 U.S.C. 154(b) by 1251 days.

(21) Appl. No.: 12/358,998

(22) Filed: Jan. 23, 2009

Related U.S. Application Data

(60) Provisional application No. 61/023,683, filed on Jan. 25, 2008.

(51) Int. Cl.
*A61B 5/08* (2006.01)

(52) U.S. Cl.
USPC .......................................................... 600/484

(58) Field of Classification Search
USPC .......................................................... 600/484
See application file for complete search history.

(56) References Cited

U.S. PATENT DOCUMENTS

| | | | | |
|---|---|---|---|---|
| 4,958,638 | A * | 9/1990 | Sharpe et al. | 600/407 |
| 6,416,471 | B1 * | 7/2002 | Kumar et al. | 600/300 |
| 6,579,242 | B2 * | 6/2003 | Bui et al. | 600/537 |

* cited by examiner

*Primary Examiner* — Benjamin Packard

(74) *Attorney, Agent, or Firm* — Christie, Parker & Hale, LLP

(57) ABSTRACT

In accordance with the present disclosure, a method for sensing vital signs of a victim includes positioning a transmitter pod near a victim. The transmitter pod transmits a source signal. A reflected signal is created by reflecting the source signal off the victim. The source signal is directly received by a receiver that is remote from the victim and the transmitter pod. The receiver also receives the reflected signal, which is compared with the source signal. At least one vital sign is determined based on this comparison, and this vital sign is displayed. The vital sign may be the victim's heart rate or respiration rate.

17 Claims, 4 Drawing Sheets

US 8,708,919 B1

SYSTEM AND METHOD FOR REMOTELY SENSING VITAL SIGNS

RELATED APPLICATION

This application claims the benefit of U.S. Provisional Application Ser. No. 61/023,683 filed Jan. 25, 2008, entitled System and Method for Remotely Sensing Vital Signs.

TECHNICAL FIELD

The present invention relates generally to remotely determining the status of an individual, and more particularly to remotely sensing vital signs.

BACKGROUND

Many casualties on the battlefield result when medical or other rescue personnel attempt to treat or rescue a downed soldier. Also, an injured individual may be located where it is dangerous to send civilian rescue workers or other emergency first responders. It may be desirable to obtain information about the victim without exposing medical personnel to enemy fire or an otherwise hazardous environment.

Attempts to detect an individual's presence and movement with hand-held radar systems that measure the backscatter of the radar signal have been made. For example, a "Radar Flashlight" was developed by Georgia Tech Research Institute, and personnel detectors have been developed by L-3 Cyterra Inc. However, these employ single-point radar, and they may not be able to distinguish the vital signs of two victims in close proximity to each other. Also, these systems may require highly precise orientation during measurement and the radar may be unable to penetrate body armor and/or wet clothing of a victim in order to sense the victim's respiration or heart rate.

SUMMARY OF THE INVENTION

In accordance with particular embodiments of the present disclosure, a method for sensing vital signs of a victim includes positioning a transmitter pod near a victim. The transmitter pod transmits a source signal. A reflected signal is created by reflecting the source signal off the victim. The source signal is directly received by a receiver that is remote from the victim and the transmitter pod. The receiver also receives the reflected signal, which is compared with the source signal. At least one vital sign is determined based on this comparison, and this vital sign is displayed. The vital sign may be the victim's heart rate or respiration rate.

Technical advantages of particular embodiments may allow medical personnel to detect and monitor the vital signs of an injured soldier or accident victim from a safe distance. This safe distance may be particularly applicable to a battlefield where medical personnel may be located away from the threat.

Further technical advantages of some embodiments include a system that includes remote voice interaction and audio monitoring. Such capability may provide the ability to orally interrogate an injured individual and use any information received to evaluate the condition of the individual and the severity of the injuries suffered.

Reduction of path loss associated with the a radar signal may be yet a further technical advantage of some embodiments of a bi-static system of the present disclosure. Typical radar path loss or signal deterioration may be approximately $1/R^4$ with R being the range. Thus, the further the victim, the weaker the return radar signal because it drops according to $1/R^4$. Using teachings of the present disclosure the path loss may be reduced to $1/R^2$, in some embodiments, which may allow detection of vital signs by a medic that is at a much greater distance from the victim. In fact, in accordance with the teachings of the present disclosure, the medic operating the receiver may be safely located in an aircraft above the battlefield.

Still a further technical advantage of some embodiments may include the ability of a remote transmitter to act as a homing beacon to guide rescue personnel or ground or air vehicles to the victim's location.

Still further technical advantages may include the ability to penetrate body armor and damp or wet clothing with a radar signal, the ability to reduce clutter or interference, and distinguish between vital signs of multiple victims. In addition, the receiver size and the probe frequency may be independently optimized without compromising spatial resolving power.

Other technical advantages of the present disclosure may be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

A more complete understanding of embodiments of the present disclosure will be apparent from the detailed description taken in conjunction with the accompanying drawings in which.

DETAILED DESCRIPTION

Figure 1A:
FIGS. 1A and 1B illustrate combat deployment of a system for remotely sensing vital signs of a victim in accordance with an embodiment of the present invention.

In accordance with particular embodiments of the present invention, disposable transmitters and hand-held receivers may allow the collection and transmission of vital signs of a victim to a medic that is positioned a safe distance from a victim, such as a hundred meters or more. Vital signs of the victim may include the victim's heart rate, respiration rate, and blood pressure. Such a system may provide improved performance over a single-point radar system, which is a single device that emits and receives a radar signal.

In general, a marksman may fire a projectile near the location of a victim. The projectile may contain a radio frequency (RF) transmitter that emits a source signal. Some of this source signal may be reflected off the victim and modulated by the heartbeat and respiration of the victim. The signal reflected from the victim and the direct signal emitted from the transmitter in the projectile may be combined and compared in a remote receiver to generate an intermediate frequency spectrum from which information about the victim's vital signs may be extracted.

FIG. 1 illustrates an example of a system 10 for remotely sensing vital signs in accordance with an embodiment of the present disclosure. System 10 includes a transmitter pod 14 and a receiver 22. It may be used by a medic 24 to assess the condition and allow triage of a victim 16.

Figure 1B:
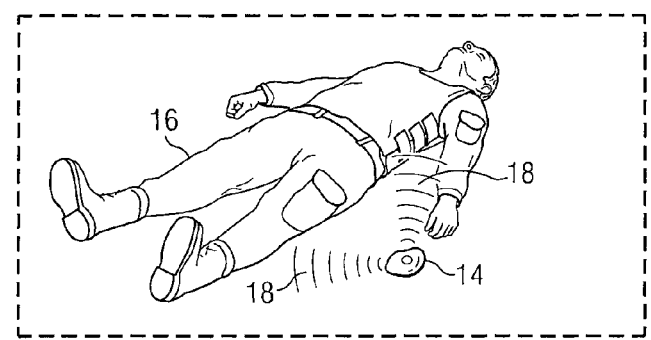

As shown in FIGS. 1A and 1B, transmitter pod 14 may be deployed by a projectile launcher 12 or thrown by hand to a point near the location of victim 16. Transmitter pod 14 may have physical characteristics that will allow it to be deployed by a firearm and remain functional after impact. Transmitter pod 14 may be referred to as a "transmitter package," a "transmitter pod," a "bean bag," or a "bean bag triage unit."

Projectile launcher 12 may be a device similar to a grenade launcher, as shown. It may be attached to a rifle or may be a stand-alone device. Transmitter pod 14 may be launched from projectile launcher 12 to a point within a few feet of victim 16. Also, if a first transmitter pod 14 is not on target, subsequent transmitter pods 14 may be launched. Alternatively, transmitter pod 14 may be dropped from a helicopter or an UAV (Unmanned Aerial Vehicle).

Transmitter pod 14 may emit source signal 18, which may be used to measure the vital signs of victim 16. Source signal 18 may be a broadcast RF signal over 2-pi steradians, which refers to a hemispherical coverage of source signal 18; however, other suitable types of signals may also be used. Source signal 18 may reflect off of victim 12 and the heartbeat and/or the movement associated with respiration of victim 12 may phase modulate source signal 18, creating reflected signal 20 (FIG. 1A). Reflected signal 20 and source signal 18, which may be a direct un-modulated signal from transmitter pod 14, may both be received and processed by receiver 22, and vital sign information may be displayed to medic 24. Due to the increased range of system 10, receiver 22 may also receive vital sign information about victim 16 even if receiver 22 is located a much greater distance from victim 16, such as in aircraft 26. In addition, reflected signal 20 and source signal 18 may be available to multiple platforms simultaneously. Thus, multiple different medics, mini-UAVs, helicopters, and other vehicles may simultaneously measure vital signs of victim 16 without interference or collaborative communication. In this manner, mission flexibility may be maximized and first response may be deployed from different directions and avenues.

With transmitter pod 14 being motionless near victim 16, clutter effects that might otherwise be induced by the motion of medic 24 may be minimized. By locating transmitter pod 14 near the victim, system 10 may have the ability to distinguish between multiple victims that are in close proximity to each other. In addition, the size of receiver 22 and the probe frequency may be independently optimized without compromising spatial resolving power.

System 10 provides significant reduction in degradation of the received signal containing vital sign information as compared to some traditional systems. Such signal degradation may be referred to as path loss. The path loss for system 10, which is a bi-static system because it includes a receiver (22) that is remote from a transmitter (14) may be approximately $1/R^2$ where R is the range from receiver 22 victim 16. Path loss associated with conventional single-point systems, which refers to a transmitter and a receiver that are not separate from each other, may be approximately $1/R^4$. Positioning transmitter pod 14 near victim 16 eliminates the path loss associated with the source signal having to travel from the medic to the victim in a single-point system. Improvements by a factor of approximately 33 in useful detection range may be achieved. For example, a medic 33 meters away using a conventional single-point radar system would receive approximately the same signal as a medic one kilometer away using system 10 in accordance with the teachings of the present disclosure. Such path loss reduction may improve signal-to-noise ratio (SiN) while lowering the required transmitter power.

Figure 2:
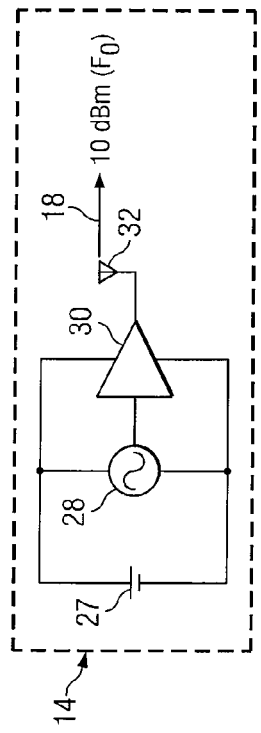
FIG. 2 is a block diagram of a basic architecture of a transmitter pod in accordance with an embodiment of the present invention.

FIG. 2 is a block diagram showing certain electronic components of an embodiment of transmitter pod 14. Transmitter pod 14 contains an oscillator 28 which generates an electronic signal that may be a continuous wave, which then passes through a pre-amplifier 30, which amplifies the electronic signal, to an antenna 32. Antenna 32 may be an omni-directional patch or a helical type antenna that transmits the resulting source signal 18. In a particular embodiment, a more sophisticated antenna 32 may be used to sense the orientation of transmitter pod 14 or multiple antennae may be configured to reduce radiation into the ground.

In certain embodiments, the signal generated by oscillator 28 could be changed to a spread spectrum or other waveforms. Oscillator 28 may be a free-running Field-Effect Transistor (FET) signal generator or it may be crystal controlled. Crystal control may provide excellent phase stability, but it may be more susceptible to the g-forces and other forces experienced at launch and impact of transmitter pod 14. A free running oscillator 28 may be mechanically robust, but it may require adequate phase noise and frequency stability to minimize source noise.

The operating frequency of source signal 18 of transmitter pod 14 may be selected for maximum penetration of the victim's 16 armor and clothing consistent with the size and power limits of transmitter pod 14 and receiver 22. Lower frequencies may penetrate wet clothes, skin, the chest cavity, and even body armor to be able to detect the shock wave of the beating heart of victim 16. As the source frequency increases by a factor of ten, the signal's ability to penetrate to reach the heart may decrease by a factor of ten. High microwave frequencies (above 15 GHz) may show significant loss through wet clothing. Thus, a low frequency may be desirable.

The source frequency should also be high enough to allow the desired signal to be extracted from the phase modulated signal received by receiver 22, however. The magnitude of the phase modulations of the source frequency increases as the source frequency increases. Thus, the detection sensitivity is increased and it may be easier to detect the phase modulation if the source signal is a higher frequency. Moreover, the electronics required to process a higher frequency may be simpler than the electronics required to process a lower frequency.

Thus, an optimal frequency may be selected that allows penetration characteristics associated with lower frequencies and the ease of detection associated with higher frequencies. In certain embodiments, the source frequency may be in the range of between 400 MHz to 3500 MHz and still penetrate wet clothing, body armor etc. Source frequencies of 450 MHz, 902 MHz, or 2400 MHz may be particularly effective at penetrating body armor, wet or dry clothing, and also penetrating the chest wall of victim 16 to interact with the heart's shock wave.

Gross motion of the body may produce a much larger amplitude and phase modulation of source signal 18 than the shock wave produced by the heart beat or motion of the chest during respiration. Thus, practically any suitable frequency may be selected to sense gross motion of the torso or limbs. Receiving higher frequencies may minimize the required aperture area for reasonable pointing accuracy. Higher frequencies may also improve antenna efficiency in transmitter pod 14. A suitable frequency may be selected by collecting data from free-space measurement of phase and amplitude modulation of frequency swept sources. Data also can be collected at W-band (80-120 GHz).

Transmitter pod 14 includes a battery 27. The power output from transmitter pod 14 may be set to meet life requirements of battery 27 and to avoid exposing victim 16 to unhealthy levels of radiation. Levels of less than a few milliwatts/cm$^2$ may be well under U.S. Food and Drug Administration (FDA) limits for microwave exposure in the 1-to-20 GHz band. In certain embodiments, a source power of approximately 10 milliwatts may be used to power transmitter pod 14.

Transmitter pod 14 may be deployed for an immediate assessment of victim 16 and may be very low cost and disposable. Battery 27 may be a flexible (thick film) lithium-ion battery may provide about 20 milliwatt hours of power per gram. In an embodiment, a small button battery (27) may provide ten times this energy capacity. Such capacity may be sufficient to power transmitter pod 14 for thirty minutes of continuous output followed by a pulsed beacon mode to guide longer term homing and recovery operations.

The weight of transmitter pod 14 may be selected in accordance with the required aerodynamics to allow it to be deployed at least 100 meters down range from medic 24. The electronics content (flex antenna, battery, transmitter circuitry) may weigh less than thirty grams.

Figure 3:
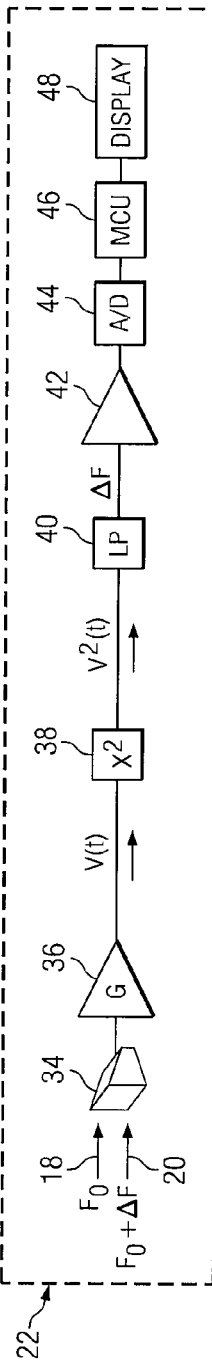
FIG. 3 is a block diagram of a basic architecture of a receiver employing a squaring circuit in accordance with an embodiment of the present invention.

FIG. 3 illustrates a block diagram of an embodiment of an architecture of receiver 22. In this embodiment, receiver 22 receives source signal 18 and reflected signal 20 and generates vital sign information of victim 16 for display. Receiver 22 includes, in this embodiment, a receiving antenna 34, a chain of low noise amplifiers 36, a squaring circuit 38, a low-pass filter 40, an amplifier 42, an analog-to-digital (A/D) converter 44, a Microcontroller Unit (MCU) 46, and a display 48; however other suitable components may be used for receiver 22.

Receiver 22 may use a homodyne architecture and include receiving antenna 34; however, other architectures may also be used. In this embodiment, receiving antenna 34 is a dipole antenna; however, other types of antennas may be used, as appropriate. Receiving antenna 34 may collect both the direct source signal 18 from transmitter pod 14 and the phase modulated signal 20 that is reflected off of victim 16. A line-of-sight signal level of about −58 dBm may be received from a 10 milliwatt source at a range of 100 meters considering a reasonable amount of gain of receiving antenna 34 and transmitter antenna 32. These two signals may be amplified by a chain of one or more low noise amplifiers 36 and passed to squaring circuit 38. Squaring circuit 38 may square the incoming voltage.

The output from squaring circuit 38 may be passed to low-pass filter 40. The output of low-pass filter 40, which carries the vital sign information, may be amplified by amplifier 42, digitized by A/D converter 44, and processed by Microcontroller Unit (MCU) 46 to extract the heart rate and respiration rate of victim 16. This data may be presented on display 48. MCU 46 may include any processor operable to process signals and extract vital sign information. Such information may also be stored in memory associated with MCU 46.

Receiver 22 may use disposable or rechargeable AA batteries. Four AA batteries (18 Watt-hours) may be able to operate receiver 22 for one week of intermittent use. The weight of receiver 22 may be minimized by using electroplated plastic for the receiving antenna 34 and flexible printed circuit boards for the electronics.

Transmitter pod 14 emits source signal 18 as a single frequency tone. For this source type and without loss of generality source signal 18 ($S_0(t)$) received directly from transmitter pod 14 by receiver 22 can be represented as a sinusoid of the form $$So(t)=Ao*\sin(2\pi ft+\theta) \quad (1)$$

where Ao is the amplitude of the signal collected by the receiver antenna 34, f is the frequency of source signal 18, t is time, and θ is the relative phase of source signal 18. The phase of source signal 18 will change with changing range of transmitter pod 14 to receiver 22. If the separation between transmitter pod 14 and receiver is fixed, and if transmitter pod 14 is stable in frequency over time, then the phase offset θ will be constant in time.

The net signal (reflected signal 20) received by receiver 22 due to signals reflected from victim 16 may contain signals associated with reflection from the clothing, skin, bones, and internal organs of victim 16. Such parts of victim 16 that are not in relative motion with respect to transmitter pod 14 and receiver 22 will reflect a portion of the incident source signal 18 and add a shift in the phase of reflected signal 20. This phase will be fixed if the range from transmitter pod 14 to victim 16 and the range from victim 16 to receiver 22 do not change.

Parts of victim 16 that are in relative motion, such as the beating heart, will modulate the phase of reflected signal 20 since the range between transmitter pod 14 and receiver 22 to these moving parts will be changing over time. The net signal (reflected signal 20) received by receiver 22 from these moving and non-moving parts of victim 16 may be expressed as a sum of sinusoids of the form $$S_{non\text{-}moving\,parts}(t)=\Sigma a_1*\sin(2\pi ft+\pi_1) \quad (2)$$

where a portion of reflected signal 20 is a sum over the non-moving parts of victim 16, and $$S_{moving\,parts}(t)=\Sigma a_j*\sin(2\pi ft+\theta j(t)) \quad (3)$$

where a portion of reflected signal 20 is a sum over the j moving parts of victim 16. θj(t) are the phase shifts in time associated with the movement of the parts of victim 16.

After amplification, the combination of source signal 18, received directly from transmitter pod 14, and reflected signal 20, received from energy reflected and/or modulated by victim 16, may be passed through squaring circuit 38, as described above. The output of squaring circuit 38 can be expressed as $$[Ao*\sin(2\pi ft+\theta)+\Sigma a_i*\sin(2\pi ft+\theta_1)+\Sigma a_j*\sin(2\pi ft+\theta j(t))]^2 \quad (4)$$

This output is then passed through low-pass filter 40, so that only signals that have a low relative frequency will remain to be further amplified. The low frequency signals will be associated with the fraction of the received signal that contains the time changing phase terms θj(t) and a steady (d.c.) offset voltage. The low frequency signals are digitized by A/D converter 44 and processed by Microcontroller Unit (MCU) 46 to extract the waveforms associated with the phase modulations θj(t).

MCU 46 may perform a Fourier spectrum analysis of the filtered signal to indicate spectral components in θj(t), for example. Thus, there may be spectral components at different frequencies. For example, there may be spectral components at 1 Hz, 2 Hz, 10, Hz, 100 Hz, and other frequencies. There may be particular components that correspond to the heart rate and the breath rate of victim 16, each of which are periodic in time, such as the periodic beat of the victim's 16 heart or the rhythmic movement of his diaphragm. These spectral components in turn translate directly into a heart rate and breathing rate of victim 16.

Figure 4:
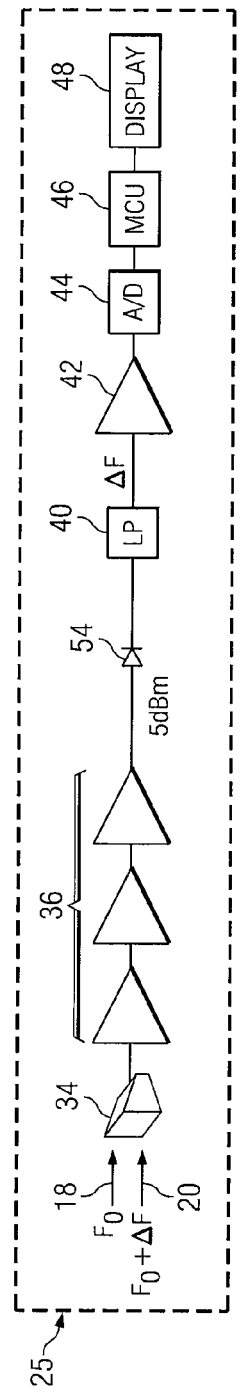
FIG. 4 is a block diagram of a basic architecture of a receiver employing a diode mixer in accordance with an embodiment of the present invention.

An alternate embodiment of the architecture of receiver 22 is illustrated in FIG. 4. In the embodiment shown in FIG. 4, a receiver 25 has squaring circuit 38 replaced by a diode mixer 54. Diode mixer 54 may provide a non-linear element that performs a squaring function. However, diode mixer 54 may add other high order terms that may need to be resolved to extract vital sign data. Each amplifier in low noise amplifier chain 36 may be in the range of 20 dB of power gain to achieve a total power gain of 60 dB for amplifier chain 36. Amplifier chain 36 may amplify the signals received by receiver 22 to a level sufficient to drive diode mixer 54 which may employ an active mixer to improve S/N and reduce amplifier gain.

The output from diode mixer 54 may be passed to low-pass filter 40. Vital signs, including heart beat and movement associated with breathing, phase modulate the source signal 18 at a very low frequency modulation. For example, 80 heartbeats per minute may be approximately 1 Hz of motion. The phase shift will be very low compared to the frequency of the source signal 18 which may be many 100's of Megahertz. Thus, low pass filter 40 may be used to block high frequency terms that do not include information useful for the detection of the vital signs of victim 16.

Figure 5:
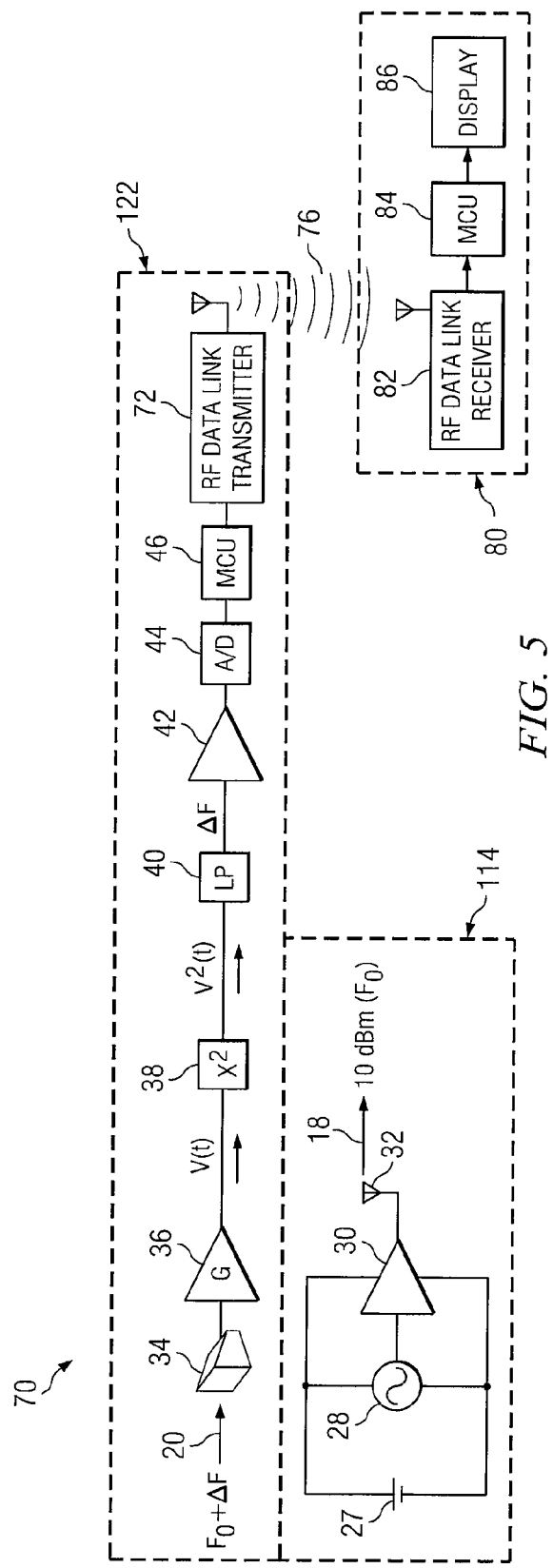
FIG. 5 is a block diagram of a combined deployable transmitter/receiver operable to communicate vital sign information to a remote medic.

In particular embodiments, rather than utilize a separate transmitter pod 14 that transmits source signal 18 and receiver 22, which in turn processes the received data, a combined transmitter/receiver pod 70 may be utilized to transmit source signal 18, process the resulting received data, and also transmit the processed data to a desired location. One embodiment of transmitter/receiver pod 70 is illustrated in FIG. 5, along with a remote unit 80 for receiving, further processing, and displaying the resulting data. Transmitter/receiver pod 70 may include a transmitter portion 114 and a receiver portion 122. Transmitter/receiver pod 70 may be a stand-alone vital sign sensor that collects vital sign information in accordance with the phase modulation signal collection and processing herein described and passes such information to an RF data link transmitter 72. Transmitter/receiver pod 70 may not directly receive source signal 18, but rather may use a copy of source signal 18 to compare to reflected signal 20.

RF data link transmitter 72 may transmit a processed signal 76, which includes extracted information regarding the vital signs of victim 16, to remote unit 80 operated by medic 24. Processed signal 76 may be transmitted using any wireless link known in the art, such as Wi-Fi, Bluetooth, etc.

Processed signal 76 may be received by a RF data link receiver 82 and further processed by MCU 84. For example, either MCU 46 or MCU 84, or both, may calculate the Fourier Transform of a sequence of digitized samples of the output of amplifier 42. This transform will provide a measure of the power spectral density of reflected signal 20. A repetitive heart rate will produce a relatively constant frequency component in the signal spectrum, which will be indicated by an increase in the amplitude of the Fourier frequency coefficient for that rhythm. The frequency of breathing will typically be less than the heart rate, and this rhythm will have a strong Fourier frequency coefficient but at a different frequency.

This vital sign information about victim 16 may be presented to medic 24 on display 86. Because receiver portion 122 is remotely deployed and its location is fixed, clutter that would otherwise need to be filtered out if receiver portion 122 was held by medic 24 may be reduced or eliminated.

In certain embodiments, processed signal 76 may be transmitted to remote unit 80 after passing through A/D converter 44 and further processing of the signal may occur at MCU 84 of remote unit 80. Still other embodiments may include A/D converter 44 as a part of remote unit 80, such that processed signal 76 may be transmitted after passing through low-pass filter 42.

Figure 6A:
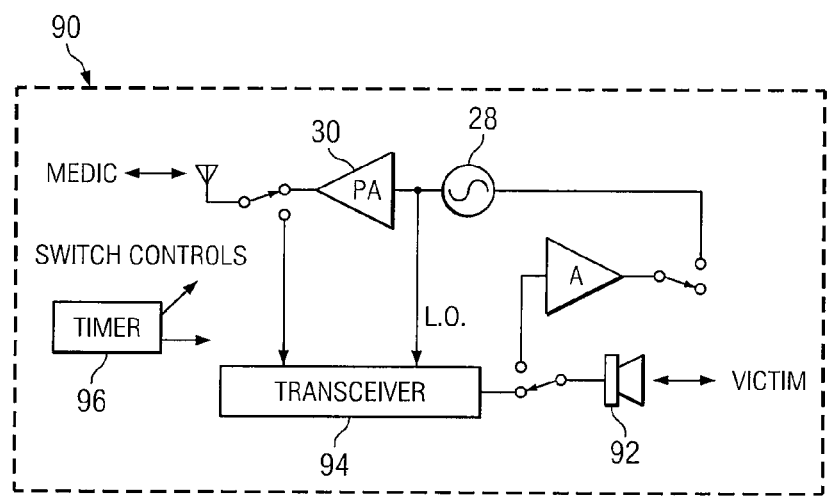
FIGS. 6A and 6B are block diagrams of a basic architecture of a transmitter pod including a two-way voice transceiver in accordance with an embodiment of the present invention.

In particular embodiments of system 10, a two-way voice transceiver 94 may be integrated into transmitter pod 14 to allow medic 24 to query victim 16 to determine his or her level of awareness and responsiveness. FIG. 6A shows an embodiment of an audio transceiver/transmitter pod 90 that may be deployed near a victim 16 similar to transmitter pod 14, and will also allow voice communication. Audio transceiver/transmitter pod 90 may include the architecture of transmitter pod 14 as illustrated in FIG. 2 for transmission of a source signal similar to source signal 18. It also includes a two-way voice transceiver 94 to allow voice communication between victim 16 and medic 24. Audio transceiver/transmitter pod 90 may also include horn 92, which may be a piezoelectric microphone/loud speaker.

As shown in FIG. 6A, oscillator 28 may generate source signal 18 and also provide the local oscillator for two-way voice transceiver 94. Thus, source signal 18 may be time multiplexed allowing a period where audio transceiver/transmitter pod 90 operates similar to transmitter pod 14 and emits source signal 18 and a period where source signal 18 is not emitted, but activation of two-way voice transceiver 94 allows verbal interrogation of victim 16.

Figure 6B:
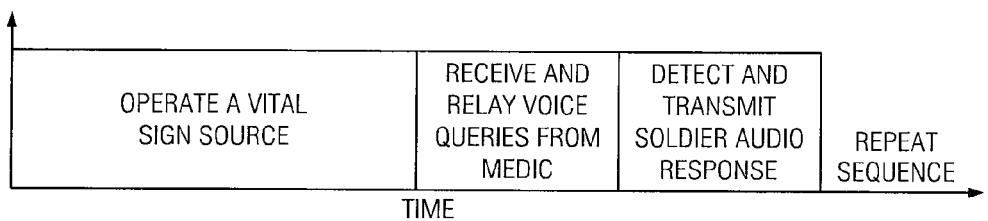

A timer 96 may switch the system mode from a vital sign source mode to a voice transceiver mode resulting in the sequence shown in FIG. 6B. Responses may be relayed back to medic 24 using two-way voice transceiver 94. In certain embodiments, verbal interrogation of victim 16 may be accomplished by including two-way voice transceiver 94 in a separate pod that does not emit source signal 18.

As illustrated in FIG. 6B, audio transceiver/transmitter pod 90 may automatically cycle through a vital sign source mode and a voice transceiver mode, and may lock into voice transceiver mode when a signal is received from medic 24. To support this functionality, receiver 22 may include a transmitter set to the frequency of oscillator 28. Receiver 22 may also include a circuit that can be switched to receive from horn 92 when required.

In alternate embodiments, sonar may be used for heart and respiration monitoring due to the close proximity of transmitter pod 14 to victim 16. The speed of sound is roughly 1 millionth that of radio waves. The wavelength of a 10 KHz sound wave is the same as that of a 10 GHz radar signal—about 3 cm. Piezoelectric microphone and loud speaker 92 used for voice interaction may also serve as the transducer for an ultrasonic sensor. Sound may sufficiently penetrate through armor and the chest wall. However, loss of ultrasound may result as it travels through the air and also from noise from ambient sources of sound clutter.

Using sonar to detect vital signs may require some processing to occur within transmitter pod 14 to allow the vital sign information to be returned to medic 24 via a radio link. Integrating a complete Sonar sensor into transmitter pod 14 may add complexity but may also simplify sensor processing because the motionless sensor is physically positioned near the victim 16.

Although the present invention and its advantages have been described in detail, it should be understood that various changes, substitutions, and alterations can be made therein without departing from the spirit and scope of the invention as defined by the appended claims.

What is claimed is:

1. A system for sensing vital signs of a victim comprising:
a projectile configured to be launched or thrown near the victim, the projectile including a transmitter pod operable to transmit a source signal;
a receiver configured to remotely receive the source signal from the transmitter pod when the transmitter pod is launched or thrown near the victim and to receive the source signal reflected off the victim, the reflected signal comprising a phase modulation of the source signal; and
the receiver comprising a processor operable to extract information regarding at least one vital sign of the victim from the remotely received source signal and the reflected signal, by combining and comparing the remotely received source signal and the reflected signal.

2. The system of claim 1, wherein the receiver further comprises a display device operable to display the information regarding the at least one vital sign of the victim to a user.

3. The system of claim 1, wherein the source signal is phase modulated by a heartbeat or a movement of a diaphragm of the victim.

4. The system of claim 3, wherein the at least one vital sign is a heart rate of the victim.

5. The system of claim 3, wherein the at least one vital sign is a respiration rate of the victim.

6. The system of claim 2, wherein the transmitter pod further comprises an oscillator operable to produce the source signal, the source signal being a continuous wave at a radio frequency greater than or equal to 400 Megahertz and less than or equal to 3500 Megahertz.

7. The system of claim 6, further comprising a two-way voice transceiver, the oscillator being operable to generate a clock signal for the two-way voice transceiver at the radio frequency.

8. The system of claim 7, further comprising a timer switch operable to automatically switch from a first phase of a cycle comprising transmitting the source signal, to a second phase of the cycle comprising receiving a voice command, to a third phase of the cycle comprising detecting and transmitting an audio response.

9. The system of claim 1, wherein the receiver comprises a squaring circuit operable to square an incoming voltage.

10. The system of claim 1, wherein the receiver comprises a diode mixer operable to provide a squaring function.

11. A system for sensing vital signs of a victim, comprising:
a pod configured to be launched from a distance to a vicinity of the victim and to transmit a source signal;
the pod operable to receive the source signal reflected off the victim, the reflected signal comprising a phase modulation of the source signal by a heart beat or a movement of a diaphragm of the victim; and
the pod further comprising a data link transmitter operable to wirelessly communicate information regarding at least one vital sign of the victim, the information being based on the reflected signal and a copy of the source signal.

12. The system of claim 11, wherein the pod further comprises a processor operable to extract information regarding the at least one vital sign of the victim from the reflected signal.

13. The system of claim 1, further comprising a projectile launcher for launching projectile.

14. The system of claim 13, wherein the projectile launcher is located in an aircraft.

15. The system of claim 1, wherein the transmitter includes a homing beacon to identify a location of the victim.

16. The system of claim 11, further comprising a two-way voice transceiver.

17. The system of claim 1, wherein the receiver is located in an aircraft.

* * * * *